United States Patent
Goto et al.

(10) Patent No.: US 9,713,449 B2
(45) Date of Patent: Jul. 25, 2017

(54) MAGNETIC RESONANCE IMAGING DEVICE AND MAGNETIC RESONANCE IMAGING METHOD

(75) Inventors: Tomohiro Goto, Tokyo (JP); Kosuke Hirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 940 days.

(21) Appl. No.: 14/008,868

(22) PCT Filed: Feb. 29, 2012

(86) PCT No.: PCT/JP2012/055102
§ 371 (c)(1),
(2), (4) Date: Sep. 30, 2013

(87) PCT Pub. No.: WO2012/137563
PCT Pub. Date: Oct. 11, 2012

(65) Prior Publication Data
US 2014/0024924 A1    Jan. 23, 2014

(30) Foreign Application Priority Data
Apr. 1, 2011 (JP) .................. 2011-082154

(51) Int. Cl.
*A61B 5/05*     (2006.01)
*A61B 5/00*     (2006.01)
(Continued)

(52) U.S. Cl.
CPC .......... *A61B 5/7285* (2013.01); *A61B 5/0037* (2013.01); *A61B 5/055* (2013.01);
(Continued)

(58) Field of Classification Search
CPC .. G01R 33/56509; A61B 5/055; A61B 5/4528
See application file for complete search history.

(56) References Cited

FOREIGN PATENT DOCUMENTS

JP      2-302248      12/1990
JP      2007-29250    2/2007
(Continued)

OTHER PUBLICATIONS

International Preliminary Report on Patentability in connection with PCT/JP2012/055102.
(Continued)

*Primary Examiner* — Joseph M Santos Rodriguez
(74) *Attorney, Agent, or Firm* — Cooper & Dunham LLP

(57) ABSTRACT

The present invention allows a subject to hold breathing at any position, and it is confirmed whether or not the breath holding is really performed in the middle of imaging to reflect its result to the imaging sequence. An image 411 showing a temporal change of respiratory displacement of the subject is generated from nuclear magnetic resonance signals acquired by executing the navigator sequence 231 repeatedly on the subject. Upon accepting from an operator a confirming operation that the operator viewing the image confirms a state of breath holding, the navigator sequence 231 is switched to the real imaging sequence 211 and the real imaging sequence is executed for a predetermined period of time. Those operations are repeated more than once. It is also possible to determine whether or not the breath holding during the imaging sequence is successfully performed, based on a difference in respiratory displacement between immediately before and immediately after the real imaging sequence.

9 Claims, 13 Drawing Sheets

(51) Int. Cl.
  *A61B 5/055* (2006.01)
  *A61B 5/11* (2006.01)
  *A61B 5/113* (2006.01)
  *G01R 33/567* (2006.01)
  *G01R 33/565* (2006.01)
(52) U.S. Cl.
  CPC ............ *A61B 5/113* (2013.01); *A61B 5/1128* (2013.01); *G01R 33/5676* (2013.01); *G01R 33/56509* (2013.01); *A61B 5/7207* (2013.01)

(56) References Cited

FOREIGN PATENT DOCUMENTS

| | | |
|---|---|---|
| JP | 2007-75387 | 3/2007 |
| JP | 2008-148806 | 7/2008 |
| JP | 2008-148919 | 7/2008 |
| JP | 2010-142423 | 7/2010 |
| JP | 2010-178895 | 8/2010 |
| WO | WO2010-150718 | 12/2010 |

OTHER PUBLICATIONS

Mar. 1, 2016 Japanese official action in connection with Japanese patent application No. JP2013-508796.
International Search Report in PCT/JP2012/055102.

MAGNETIC RESONANCE IMAGING DEVICE AND MAGNETIC RESONANCE IMAGING METHOD

TECHNICAL FIELD

The present invention relates to a magnetic resonance imaging (hereinafter, referred to as "MRI") device for measuring a nuclear magnetic resonance (hereinafter, referred to as "NMR") from hydrogen, phosphorus, and the like, within a subject, so as to create an image such as a nuclear density distribution and a relaxation time distribution.

BACKGROUND ART

Upon taking an image of a chest region or an abdominal region by the use of the MRI device, it is often found to be a problem that an artifact occurs due to respiratory movement. There are methods for preventing the artifact caused by the respiratory movement, such as a breath-hold imaging method and a method using a navigator sequence, as described in the patent document 1, for instance.

The breath-hold imaging is the simplest method, and it is in widespread clinical use. In the breath-hold imaging, the imaging time for one time is limited to a duration that allows suspension of respirations (around 15 seconds at longest). Therefore, in the case of multi-slice imaging, or the like, which requires long imaging time, the breath-hold imaging is separated into multiple imaging operations.

There are known following methods which use the navigator sequence; a method for monitoring a position of the diaphragm without breath holding in the navigator sequence and an imaging sequence is executed during a period when the position of the diaphragm is included in a predetermined gate window; and a method for monitoring the position of diaphragm in the navigator sequence, and when the diaphragm reaches a predetermined position, the subject is instructed to hold breathing, and the imaging sequence is executed during the breath holding period. Also in the cases above, the imaging sequence is executed, being separated into multiple operations, until acquiring a predetermined number of echo signals that are necessary for reconstructing an image.

The patent document 1 further discloses a method for executing the imaging sequence after it is confirmed that the position of the diaphragm being detected in the navigator sequence has entered the predetermined gate window, a method for executing a simplified body motion monitoring even during the imaging sequence to check whether or not the position of the diaphragm is within the gate window, and a method for detecting the position of the diaphragm not only before the imaging sequence but also immediately thereafter so as to check whether or not the position of the diaphragm is within the gate window. This configuration prevents execution of the imaging sequence outside the gate window, thereby enhancing efficiency in acquiring echo signals.

In addition, echo signals of the imaging sequence that is executed outside the gate window are discarded and they are not used for reconstructing the image. The patent document 1 further discloses that, in combination with the methods described above, if there is any displacement of the position of diaphragm immediately before the imaging sequence, between the first imaging sequence and the second imaging sequence, the slice position is modified according to the displacement, so as to take an image of the same position.

The patent document 1 further discloses a method for monitoring respiratory movement by an exterior sensor instead of the navigator sequence, and executing the imaging sequence when breath holding (suspension of respiratory movement) is confirmed. Since this method uses the exterior sensor, it is possible to monitor the respiratory movement even during the imaging sequence, and an alarm display may be provided upon detecting unsteadiness in the respiratory movement.

There are examples such as the patent document 2 and the patent document 3 which disclose a technique for detecting an amount of positional displacement upon breath holding, and according to this displacement amount, a slice position, and the like, are modified upon imaging.

PRIOR ART DOCUMENT

Patent Document

Patent Document 1
Japanese Unexamined Patent Application Publication No. 2007-29250
Patent Document 2
Japanese Unexamined Patent Application Publication No. 2008-148918
Patent Document 3
Japanese Unexamined Patent Application Publication No. 2007-75387

DISCLOSURE OF THE INVENTION

Problem to be Solved by the Invention

Any of the conventional imaging methods as described above uses echo signals obtained only when the diaphragm is positioned within a predetermined gate window, in order to reconstruct an image. Therefore, there is a problem that a long imaging time is necessary until obtaining a required number of echo signals for the image reconstruction. The method for holding breath in the state where the diaphragm is positioned within the predetermined gate window may reduce the imaging time relative to the case where there is no breath holding, but the breath holding operation along with positioning the diaphragm to be in the gate window has to be repeated more than once. Here, it depends on each subject, breath holding in the middle of inspiration is easy or breath holding in the middle of expiration is easy, and it also depends on each subject which position is comfortable for breath holding. Therefore, it is not easy for the subject to repeat the breath holding at the gate window position and timing being directed. In some cases, clinically, the subject may be required to practice the breath holding in advance.

Further in the conventional imaging method, it is not possible for an operator to know in the middle of the imaging operation whether or not the subject is really in the breath holding state. The patent document 1 further discloses a method for executing simplified monitoring of body movement in the middle of executing the imaging sequence, the monitoring setting a gradient magnetic field in the phase encoding to be zero. This method, however, results in extending the time for executing the imaging sequence, by the time for executing the simplified monitoring of the body movement. The method for constantly monitoring the respiratory movement by equipping the subject with the exterior sensor, allows the operator to be aware of a failure in breath holding by an alarm, but it is not possible to reflect the failure to the sequence in the middle of the imaging sequence. Therefore, if any artifact is found after the end of imaging, there is no other way than a retake.

An object of the present invention is to provide a technique in an imaging operation by an MRI device, the technique allowing the subject to hold breathing at any position, checking whether or not the breath holding is really performed in the middle of imaging, and reflecting a result of the checking to the imaging sequence.

Means to Solve the Problem

In order to achieve the object above, the present invention executes pulse sequences including a navigator sequence for detecting respiratory displacement of a subject, and a real imaging sequence for taking an image of the subject. In the present invention, an image is generated to show a temporal change of the respiratory displacement based on nuclear magnetic resonance signals acquired by executing the navigator sequence, and thus generated image is displayed. When an operator viewing this image confirms the breath holding state, this confirming operation is accepted, and then the real imaging sequence is executed.

Effect of the Invention

According to the present invention, in the imaging operation using the MRI device, a subject is allowed to hold breathing at any position, and it is possible to check in the middle of imaging, whether or not the breath holding is really performed and reflect the checking result to the imaging sequence.

BEST MODE FOR CARRYING OUT THE INVENTION

Figure 1:
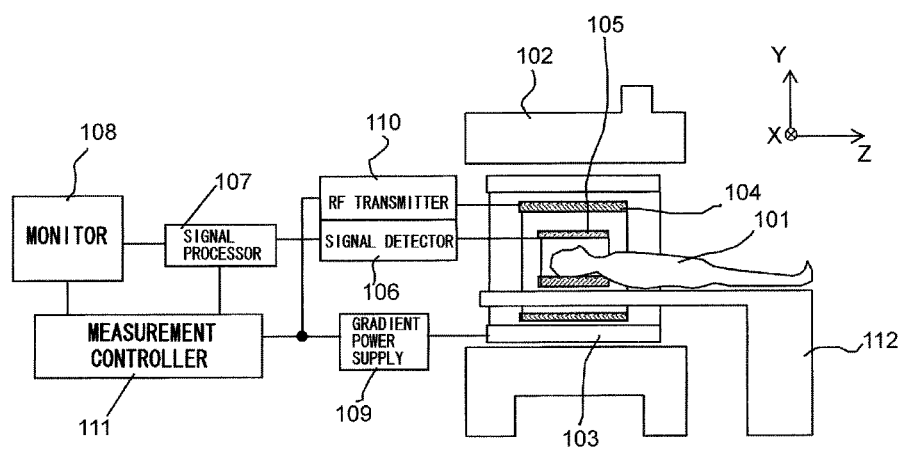
FIG. 1 is a block diagram illustrating an overall structure of the MRI device according to the present invention.

An MRI device of the present invention includes a static magnetic field generator for generating a static magnetic field in imaging space where a subject is placed, a gradient magnetic field generator for applying a gradient magnetic field to the imaging space, a radio frequency emitter for irradiating the imaging space with an RF magnetic field pulse, a receiver for receiving a nuclear magnetic resonance signal generated from the subject, and a controller for controlling the gradient magnetic field generator, the radio frequency emitter, and the receiver, so as to execute predetermined pulse sequences. The pulse sequences described above include a navigator sequence for detecting respiratory displacement of the subject, and a real imaging sequence for taking an image of the subject. The controller includes a respiratory movement image generator, a breath-hold confirmation accepting part, and a real imaging execution part. The respiratory movement image generator generates and displays an image showing a temporal change of respiratory displacement based on nuclear magnetic resonance signals acquired by executing the navigator sequence. The breath-hold confirmation accepting part accepts a confirming operation when the operator viewing the image displayed by the respiratory movement image generator confirms the state of breath holding. The real imaging execution part executes the real imaging sequence at the timing when the breath-hold confirmation accepting part accepts the confirming operation.

The controller may be configured in such a manner that the operations by the respiratory movement image generator, the breath-hold confirmation accepting part, and the real imaging execution part, are repeated more than once in this order, respectively, until all the nuclear magnetic resonance signals necessary for reconstructing an image of a predetermined imaging area, are obtained by the real imaging sequence.

It is further possible for the controller to obtain a difference in respiratory displacement acquired immediately before each of the real imaging sequences being repeated more than once, and according to this difference, an imaging position of the second and subsequent real imaging sequences may be adjusted.

The controller may also be provided with a retake accepting part. The retake accepting part reconstructs and displays an image based on the nuclear magnetic resonance signals acquired in each real imaging sequence that is performed repeatedly more than once, and accepts an instruction from the operator whether or not the real imaging sequence for the present time is retried. Upon accepting the instruction to perform a retake, the retake accepting part sets the imaging position of the real imaging sequence for the present time as the imaging position of the next real imaging sequence.

The retake accepting part obtains and displays a difference in respiratory displacement between immediately before and immediately after the real imaging sequence for each real imaging sequence repeated more than once, and accepts from the operator, an instruction whether or not a retake is performed as to the real imaging sequence for the present time.

The retake accepting part determines whether or not the breath is suspended successfully during the real imaging sequence for each real imaging sequence performed repeatedly more than once. If it is determined that the breath holding fails, the retake accepting part may set the imaging position of the real imaging sequence for the present time as the imaging position of the real imaging sequence for the next time. By way of example, a difference in respiratory displacement between immediately before and immediately after the real imaging sequence is obtained, and if the difference in respiratory displacement is larger than a predetermined threshold, it is determined that the breath holding during the real imaging sequence has failed.

The present invention also provides a magnetic resonance imaging method. This magnetic resonance imaging method repeats a first step and a second step more than once until obtaining all the nuclear magnetic resonance signals necessary for reconstructing an image of a predetermined imaging area, by the real imaging sequence; the first step generating and displaying an image showing a temporal change of the respiratory displacement of the subject based on the nuclear magnetic resonance signals acquired by executing the navigator sequence repeatedly on the subject, and the second step switching from the navigator sequence to the real imaging sequence to perform the real imaging sequence for a predetermined period of time, upon accepting from the operator a confirming operation that the operator viewing the image confirms the breath holding state.

Whether the breath holding is successfully performed or not during the real imaging sequence may be determined based on the difference in respiratory displacement between immediately before and immediately after the real imaging sequence. If it is determined that the breath holding has failed, a retake is performed by the next real imaging sequence at the imaging position of the real imaging sequence for the present time.

In the present invention as described above, a gate window is not used, and therefore the subject is allowed to perform breath holding at any position. In addition, the operator is allowed to confirm that breathing of the subject is in the state of suspended, before starting the real imaging sequence. Even in the case where the breath holding fails, it is possible to reacquire minimal data easily. In addition, even in the case where there is respiratory displacement between the breath holding points, compensation for slice displacement corresponding to the displacement difference may be performed.

One embodiment of the present invention will be explained specifically.

Firstly, with reference to FIG. 1, a configuration of the MRI device according to the present embodiment will be explained. The MRI device is provided with a magnet 102 for generating a static magnetic field in an imaging area where a portion to be imaged of a subject 101 is placed, a gradient coil 103 for generating a gradient magnetic field in the imaging area, a radio frequency (RF) coil 104 for generating an RF magnetic field in the imaging area, and an RF probe 105 for receiving NMR signals generated from the subject 101. The MRI device is further provided with a bed 112, an RF transmitter 110, a signal detector 106, a gradient power supply 109, a signal processor 107, a measurement controller 111, and a monitor 108.

The gradient coil 103 includes coils for generating gradient magnetic fields in three directions, X, Y and Z, respectively. The gradient coil 103 is connected to a gradient power supply 109. The gradient coil 103 generates gradient magnetic fields respectively, in X, Y, and Z, in response to a signal received from the gradient power supply 109. The RF coil 104 is connected to the RF transmitter 110, and generates an RF magnetic field in response to the signal from the RF transmitter 110. The RF probe 105 is connected to the signal detector 106, and the signal detector 106 detects the NMR signal received by the RF probe 105.

The signal processor 107 processes the signal detected by the signal detector 106 and converts the signal into an image signal according to a computation. The monitor 108 displays the image.

The measurement controller 111 controls the operations of the gradient power supply 109, the RF transmitter 110, and the signal detector 106. A time chart for those controls is generally referred to as a pulse sequence. The bed 112 is provided for laying the subject 101 thereon.

A target to be imaged by the MRI device, widely used clinically, is proton being a main component material of the portion to be imaged of the subject 101. A space distribution of the proton density or a space distribution of relaxation phenomenon of the excitation state is created as an image, thereby obtaining a two-dimensional or three-dimensional image of morphological features of a human body such as a head region, an abdominal region, and four limbs, or functions thereof.

Next, a principle of an imaging method of the MRI device will be simply explained. A gradient magnetic field in a predetermined direction is applied from the gradient coil 103 to the subject 101 placed in the imaging space to which the static magnetic field is applied from the magnet 102, thereby selecting a predetermined slice, and applying a radio frequency pulse from the RF coil 104 to excite nuclear magnetism. Phase encoding being different for each gradient magnetic field is given, and an NMR signal (echo signal) obtained by each phase encoding is detected. On this occasion, a readout gradient magnetic field is applied if required. The number of phase encoding per image is selected typically from the values such as 128, 256, and 512. Each echo signal is obtained in the form of time-series signal made up of sampling data items, typically, the number thereof being 128, 256, 512, and 1024. These data items are subjected to the two-dimensional Fourier transform, so as to create one MR image. A specific pulse sequence will be discussed later.

First Embodiment

Figure 2:
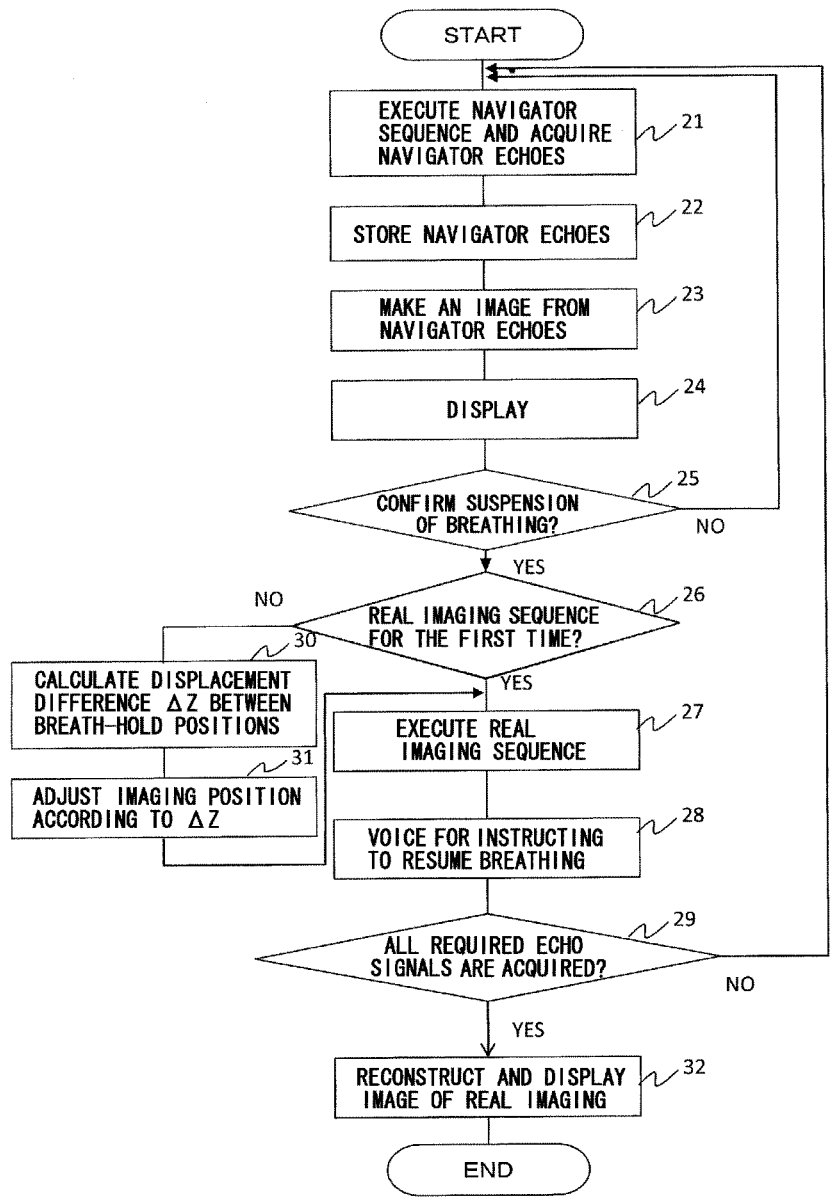
FIG. 2 is a flowchart illustrating overall processing of an imaging operation of the first embodiment.
Figure 3:
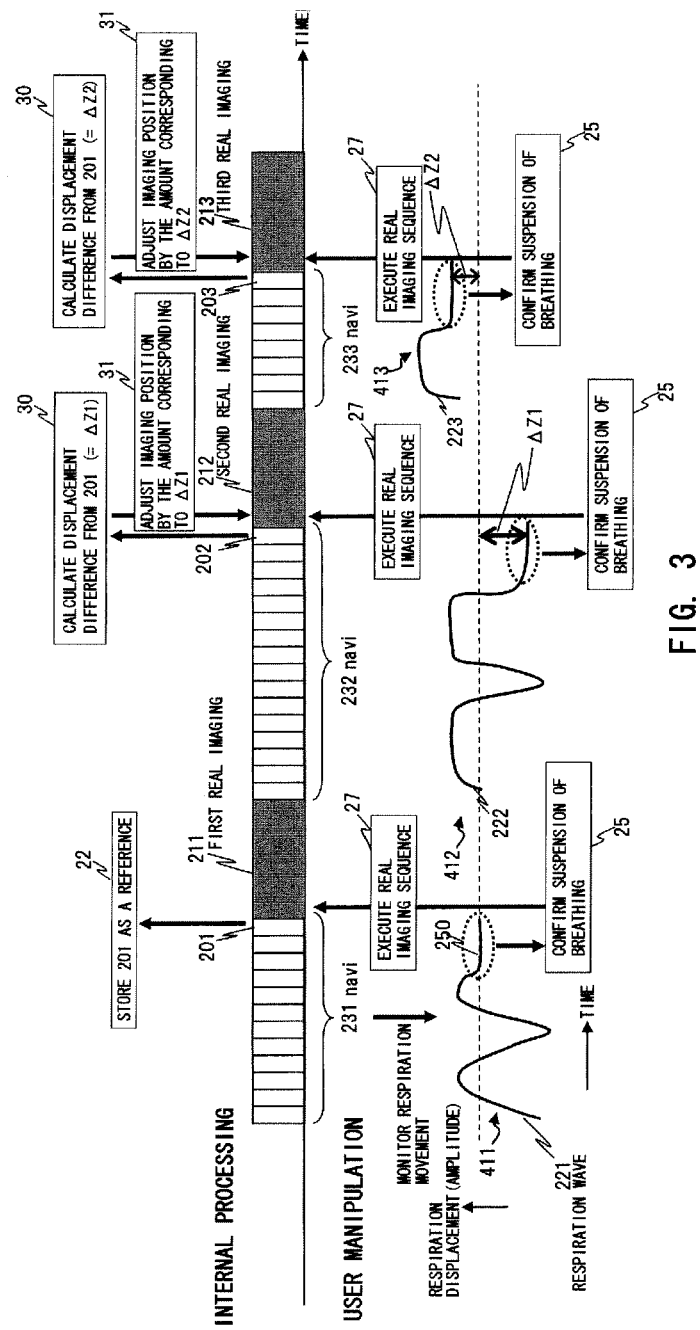
FIG. 3 illustrates a relationship in the first embodiment, among the operations within the MRI device, such as a navigator sequence and a real imaging sequence, respiratory displacement detected by navigator echoes, and manipulations by a user.

With reference to FIG. 2, FIG. 3, etc., an explanation will be made as to an operation of each part upon taking an image, in the first embodiment of the present invention. FIG. 2 is a flowchart illustrating an overall operation upon taking an image, and FIG. 3 illustrates a relationship among operations within the MRI device such as a navigator sequence and a real imaging sequence, respiratory displacement detected by navigator echoes, and manipulations by a user.

Figure 4:
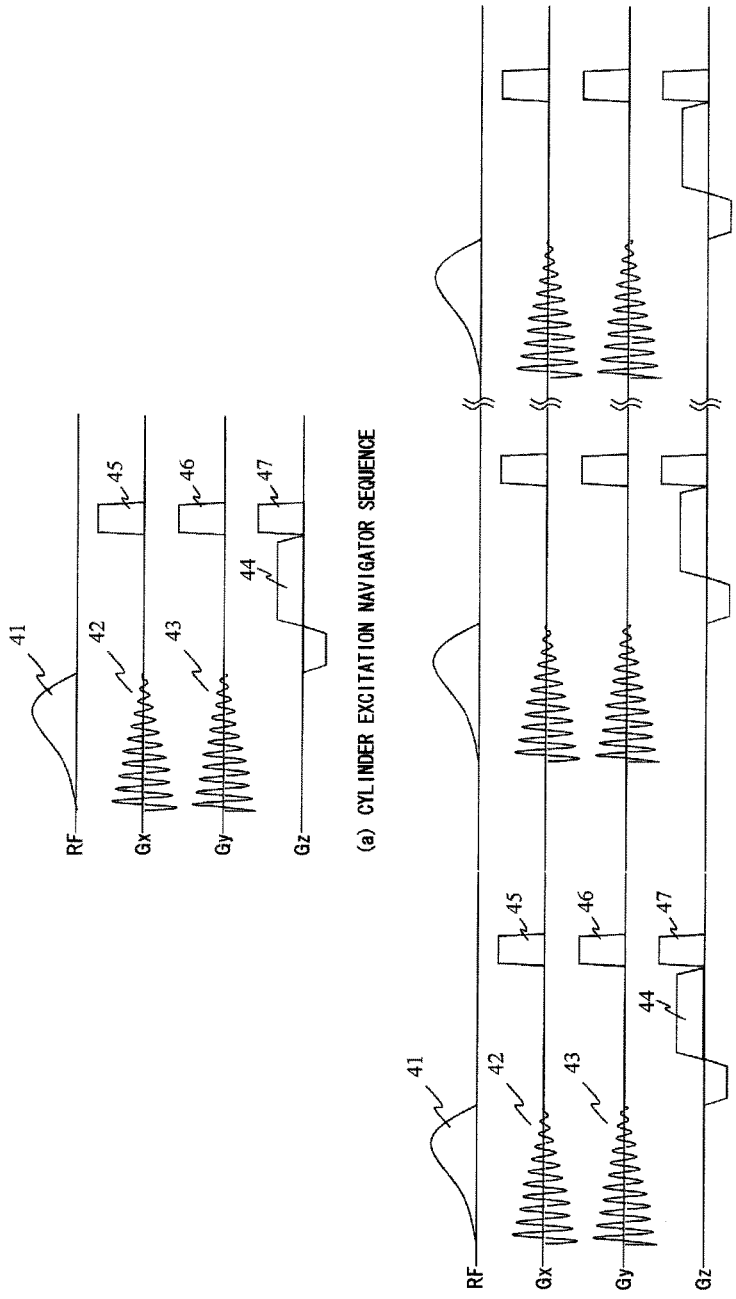
FIG. 4(a) illustrates the navigator sequence of the first embodiment.
FIG. 4(b) illustrates continuous navigator sequence.

The measurement controller 111 reads and executes programs stored in the build-in memory, thereby controlling each part as shown in the flow of FIG. 2, and executing the imaging. Specifically, the measurement controller 111 controls each part, and executes the navigator sequence as shown in FIG. 4(a), thereby acquiring navigator echoes (step 21). According to this operation, respiratory movement of the subject is monitored. The position for acquiring the navigator echoes is optional, as far as it is a portion which moves by breathing, such as the diaphragm and abdominal wall. Specifically, by applying an RF pulse 41 while applying a gradient pulse Gx42 in the X-axis direction and a gradient pulse Gy43 in the Y-axis direction, thereby selectively exciting a column-like region along the body axis direction (Z-axis direction), and a readout gradient pulse Gz44 is applied in the Z-axis direction, thereby acquiring a navigator echo. Thereafter, crusher gradient pulses Gx45, Gy46, and Gz47 are applied in the XYZ-axis directions, respectively, thereby dispersing magnetization.

Figure 5:
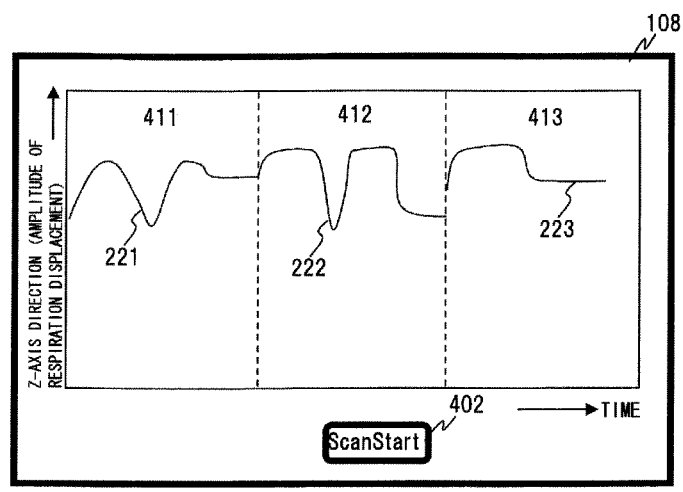
FIG. 5 illustrates an image of respiratory waves displayed on the monitor 108 and the "Scan Start" button 402 manipulated by the operator who confirmed the breath holding in the first embodiment.

The navigator echoes being acquired are stored in the memory within the measurement controller 111, and simultaneously the signal processor 107 subjects the navigator echoes to the Fourier transform, thereby transforming the echoes into absolute-value data (image) (steps 22 and 23). Since the navigator echoes are read out in the body axis direction, when they are transformed into absolute-value data, the absolute-value data at the position of the diaphragm, abdominal wall, or the like, indicates a large value. By way of example, as shown in FIG. 5, the absolute-value data is displayed as brightness, every time being acquired, on the screen of the monitor 108 assuming the Z-axis direction as the vertical axis and assuming the acquisition time as the horizontal axis, thereby generating and displaying an image 411 in which the displacement in the Z-axis direction represents the respiratory displacement (amplitude) (step 24).

The operator viewing the image 411 of this respiratory displacement is allowed to check a respiratory wave 221 of the subject 101. If the breath holding is not confirmed by the operator, i.e., the "Scan Start" button 402 on the screen is not manipulated (a start of the real imaging sequence 211 is not instructed), the navigator sequence is repeatedly executed according to the steps 21 to 24 as shown in FIG. 4(b) (continuous navigator sequence 231). Along therewith, creating an image from the navigator echoes is continuously repeated, whereby the respiratory wave 221 of the image 411 is sequentially displayed in the time axis direction (step 25).

The operator provides an instruction of breath holding to the subject with whatever timing, while viewing the respiratory wave 221 of the image 411. By way of example, the instruction is provided by voice. By checking the change of the respiratory wave 221 of the image 411, it is confirmed that the subject 101 actually suspends breathing. As shown in FIG. 3, when breathing is suspended, amplitude of the respiratory wave 221 becomes flat, and there occurs a region 250 being stable at a certain level, and therefore, the suspension of breathing (breath holding) is easily confirmed.

Figure 6:
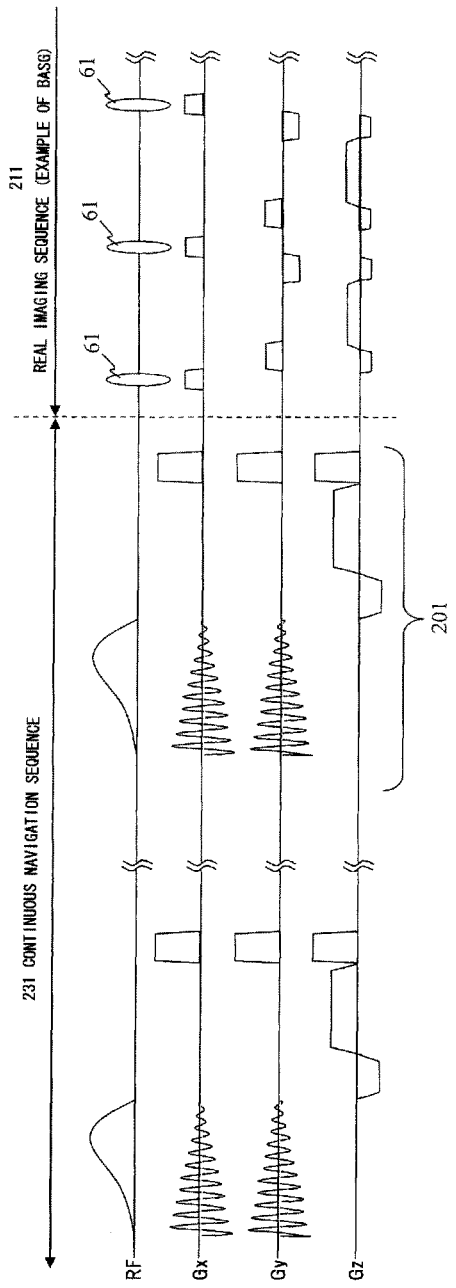
FIG. 6 illustrates switching from the continuous navigator sequence to the real imaging sequence in the first embodiment.

Upon confirming the breathing suspension, the operator manipulates the "Scan Start" button 402 on the screen, for instance, and instructs a start of the real imaging sequence 211 (step 25). Accordingly, the first real imaging sequence 211 is executed (steps 26 and 27). In other words, as shown in FIG. 6, the continuous navigator sequence 231 is terminated and the real imaging sequence 211 is executed. In the present embodiment, the real imaging is performed according to a multi-slice imaging method in which echo signals necessary for the image reconstruction of a predetermined number of slices are divided into three-time real imaging sequences 211, 212, and 213, for performing the imaging. As shown in FIG. 6, the BASG (Balanced SARGE) method is shown as an example of the real imaging sequence 211, the method applying RF pulses 61 continuously by a short repetition time (TR), thereby rendering the transverse magnetization to be in the steady state and acquiring echo signals. The imaging sequence 211, however, is not limited to the BASG method, but any desired imaging sequence may be carried out. In the real imaging sequence 211, the repeat count is defined in advance, in such a manner that the sequence ends within the time that allows the breath holding (e.g., 10 to 15 seconds).

After terminating the real imaging sequence 211, the subject 101 is instructed to resume breathing (step 28). If all the echo signals necessary for reconstructing the images of all slices are not acquired yet (step 29), the operation returns to the step 21 to execute the continuous navigator sequence 232 in order to prepare for executing the second real imaging sequence 212. The instruction for the subject to end the breath holding may be performed according to a method where prepared voice is provided automatically, or the operator may provide the instruction by his or her own voice.

In the second navigator sequence 232 from the steps 21 to 24, similar to the first navigator sequence 231, the operator confirms that the subject 101 becomes in the state of breath holding, according to the image 412 of the respiratory wave 222 being monitored by the navigator echoes (step 25), and the operator manipulates the "Scan Start" button 402, thereby starting the real imaging sequence 212.

On this occasion, before executing the second real imaging sequence 212, the operation proceeds to the step 30, and a difference $\Delta Z1$ is calculated between the respiratory displacement (amplitude) for breath holding immediately before the first real imaging sequence 211 and the respiratory displacement immediately before the second real imaging sequence 212. Difference $\Delta Z1$ in the respiratory displacement may arise easily, in such a case that breathing is suspended in the state of inspiration for the first time, and breathing is suspended in the state of expiration for the second time. Therefore, navigator echoes stored in the memory of the measurement controller 111 in the step 22 are read out, the navigator echoes being acquired immediately before the first real imaging sequence, i.e., being acquired in the last sequence 201 of the first continuous navigator sequence 231. With reference to thus readout navigator echoes, the navigator echoes acquired in the last sequence 202 of the second continuous navigator sequence 232 are subjected to comparison, thereby calculating $\Delta Z1$ quantitatively. The quantitative comparison is possible according to a general calculation, such as a method of least squares and a calculation of correlation coefficient, for instance.

This displacement difference $\Delta Z1$ represents a shift length of the diaphragm or the abdominal wall position. Therefore, if the second real imaging sequence 212 is executed in the step 27 without any change, a portion (slice) being displaced from the portion (slice) that is supposed to be imaged originally in the second real imaging sequence 212, is targeted for the imaging. Therefore, the measurement controller 111 adjusts frequency values of the gradient pulses and the RF pulses in the real imaging sequence 212 according to a predetermined computation, so that the slice of the second real imaging sequence 212 is displaced only by the distance corresponding to the displacement difference ΔZ1 being calculated quantitatively. Then, in the step 27, the real imaging sequence after the adjustment is executed. Accordingly, in the real imaging sequence 212, it is possible to acquire echo signals being associated with the slice to be originally imaged in the second real imaging sequence 212.

After the end of the second real imaging sequence 212, resuming of breathing is instructed to the subject (step 28), and if all the echo signals necessary for the image reconstruction have not been acquired yet, the operation returns to the step 21. According to the steps 21 to 24, the continuous navigator sequence 233 for the third imaging is performed, and breath holding is checked based on the image 413 of the respiratory wave 223 that is monitored by the navigator echoes (step 25). Then, difference ΔZ2 between the respiratory displacement (amplitude) of the breath holding for the first imaging and the respiratory displacement for the third imaging is calculated, and the slice position of the real imaging sequence 213 is adjusted in association with the difference Z2 in respiratory displacement (steps 30 and 31). The real imaging sequence 213 after the adjustment is executed, and echo signals are acquired (step 27). When all the echo signals necessary for image reconstruction of all the slices are acquired according to the operations above, an image is reconstructed, and displayed on the monitor 108.

As discussed above, the present embodiment allows the real imaging to be performed after the operator checks by the navigator echoes, whether or not breathing is actually suspended without using a gate window. Therefore, it is possible to avoid performing the real imaging sequence in the state where the breathing is not suspended yet, thereby preventing a retaking situation due to a failure of the breath holding, resulting in reduction of overall imaging time.

In addition, a respiratory wave detected by the navigator echoes is able to be checked on the image by the operator, and therefore, it is possible to check in the middle of imaging, whether or not the breath holding is executed. Therefore, if retaking an image is required due to the failure of the breath holding, the necessity is determined on the way of imaging, and this may reduce the time required for the imaging.

In addition, since the gate window is not used in the present embodiment, echo signals acquired outside the gate window are not discarded.

Furthermore, nonuse of the gate window in the present embodiment allows the subject to hold breathing at a desired position which is convenient for him or her, thereby reducing the burdens on the subject.

Second Embodiment

A second embodiment of the present invention will be explained. In the first embodiment, the real imaging sequence is started after the operator confirms that breath holding is actually performed, but there is a possibility that the breath-holding state may not be maintained until the end of the imaging. The second embodiment solves this problem.

Figure 7:
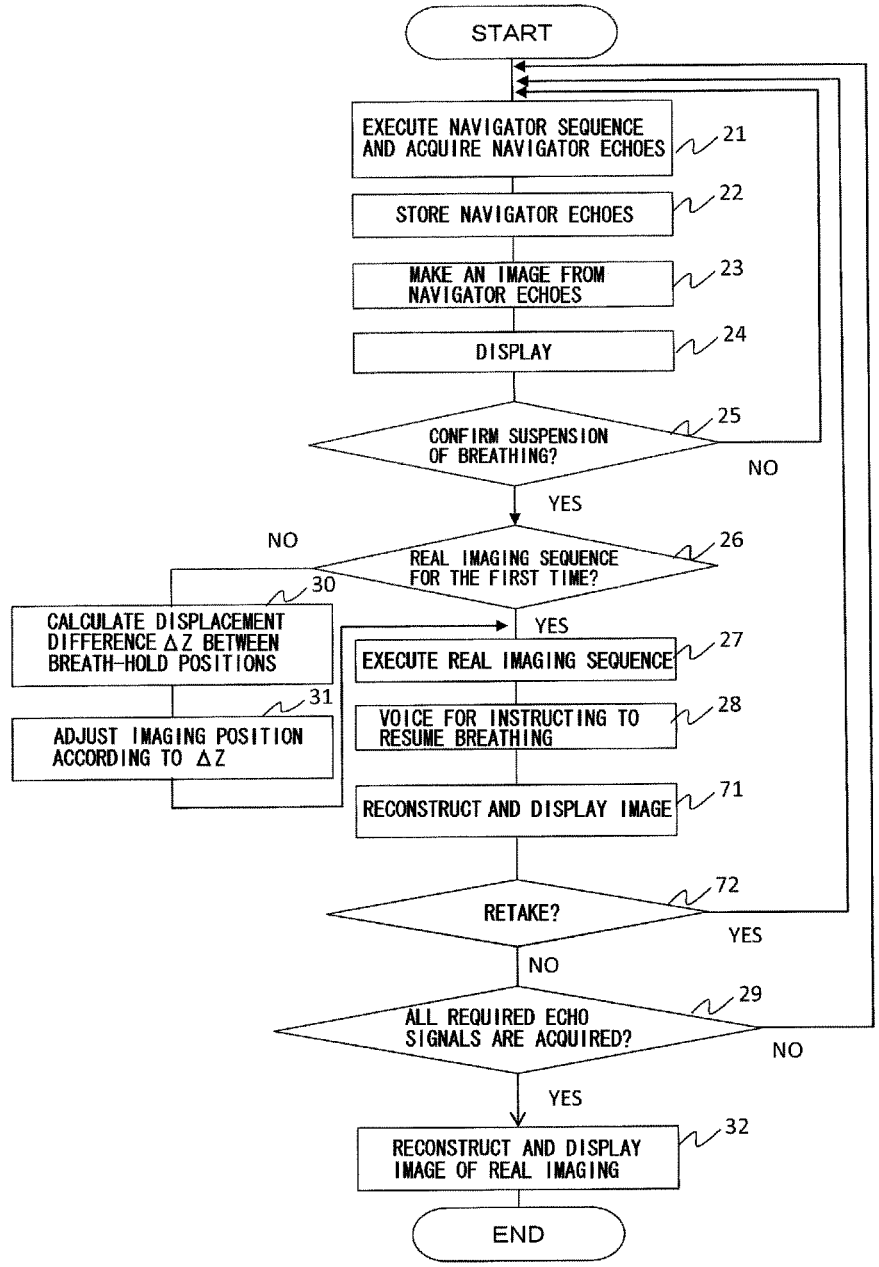
FIG. 7 is a flowchart illustrating the overall processing of the imaging operation of the second embodiment.
Figure 8:
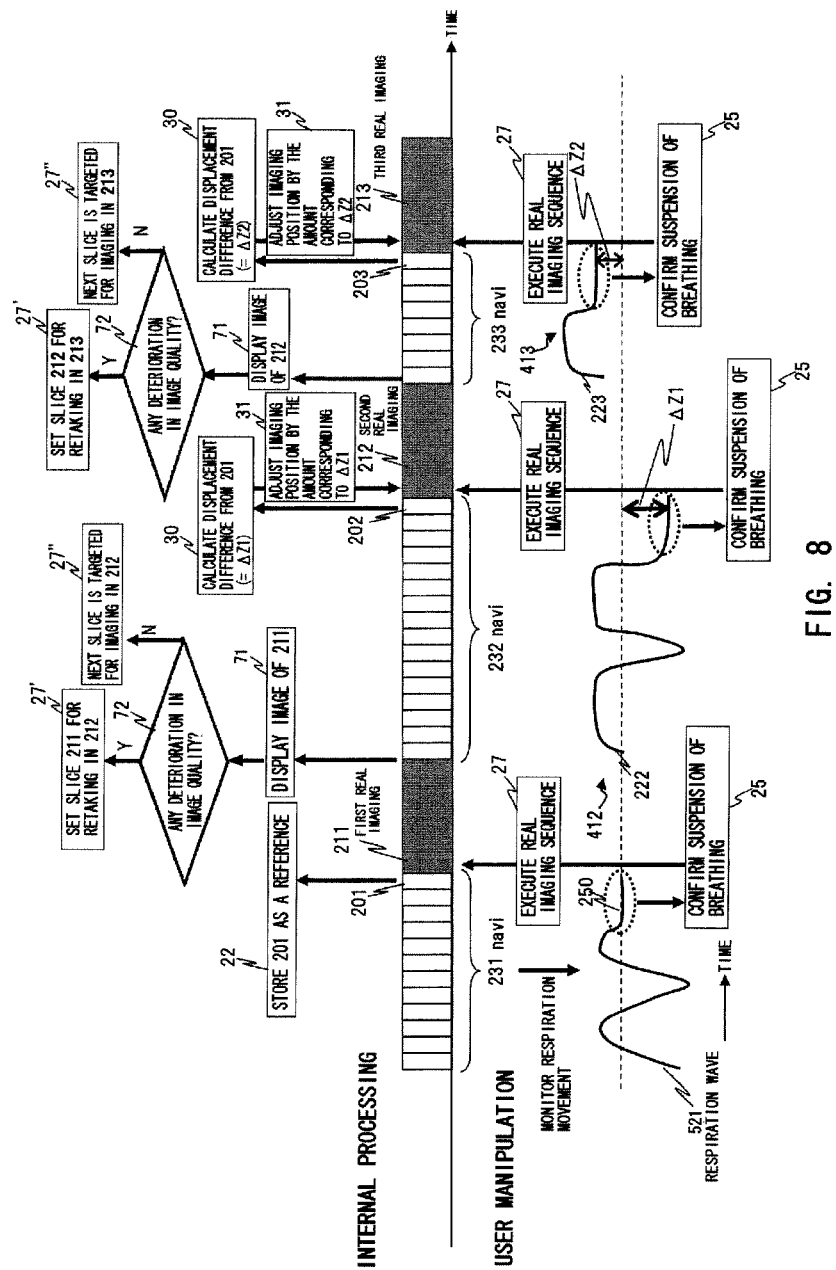
FIG. 8 illustrates a relationship in the second embodiment, among operations within the MRI device such as the navigator sequence and the real imaging sequence, respiratory displacement detected by navigator echoes, and manipulations by the user.

FIG. 7 is a flowchart illustrating an overall operation of the imaging method according to the second embodiment. FIG. 8 illustrates a relationship among operations within the device such as the navigator sequence and the real imaging sequence, respiratory displacement detected by navigator echoes, and manipulations by the user. In those figures, the constitutional elements and processing being the same as those in the first embodiment are labeled the same.

Similar to the first embodiment, the navigator sequence 231 is executed repeatedly according to the steps 21 to 25, thereby acquiring navigator echoes continuously, and displaying an image of the respiratory wave 521. Then, if the operator confirms the breath holding and instructs the real imaging, the first real imaging sequence 211 is executed in the state of breath holding. When the real imaging sequence 211 is terminated, resumption of breathing is instructed (step 28).

Figure 9:
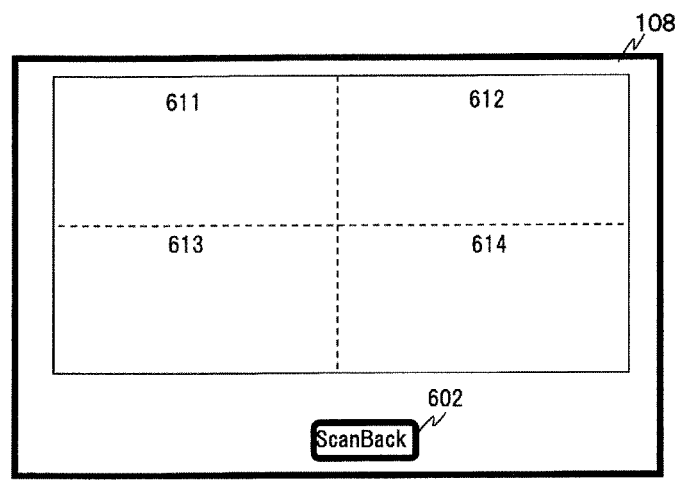
FIG. 9 illustrates on the monitor 108 in the second embodiment, display areas for displaying images such as the image 611 of the real imaging sequence, and the "Scan Back" button 602 used by the operator for instructing a retake when the operator determines that the breath holding has failed.

Here, in the second embodiment, the operation proceeds to the step 71, image reconstruction is performed by using the echo signals acquired in the first real imaging sequence 211, and a reconstructed image 611 is displayed on the monitor 108 as shown in FIG. 9. The reconstructed image 611 allows the operator to visually check whether or not the real imaging was actually in the state of breath holding. If the subject 101 fails in breath holding, a flow artifact or blurring may occur in the image 611. In the case where the operator determines by the displayed image 611 that the subject 101 failed in breath holding, the operator presses the "Scan Back" button 602 on the displayed image, thereby instructing to retake an image of the slice in the second real imaging sequence, the slice being the same as that of the first real imaging sequence (step 72).

Accordingly, the operations from the step 21 to the step 25 are performed, an image of the respiratory wave 522 is displayed, and when the operator confirms the breath holding and instructs the real imaging, the second real imaging sequence 212 is executed in the state of breath holding. In the second real imaging sequence 212, an image of the slice is taken, being the same as the slice in the first real imaging sequence 211 as to which a retake is instructed in the step 72. It is to be noted that before the second imaging sequence, displacement difference ΔZ1 at the position upon breath holding is obtained in the steps 30 and 31 so as to adjust the imaging position, and this operation is similar to the first embodiment.

Similarly, in the subsequent imaging, images are reconstructed from the echo signals obtained after every real imaging sequence, and the reconstructed images 612 to 619 are displayed sequentially being arranged in the screen window on the monitor 108 (step 71). The operator views those images, and determines whether or not a retake is necessary (step 72). Those steps are repeated, and when all the echo signals necessary for the image reconstruction are acquired (step 29), all the echo signals obtained in the real imaging are used to reconstruct an image, and the image is displayed (step 32).

As thus described, in the second embodiment, the operator is allowed to confirm, sequentially by the reconstructed images, that the breath holding is performed during the real imaging, in addition to the imaging operation of the first embodiment. This ensures that the breath holding is performed and it is possible to obtain an image without an artifact due to the failure in breath holding. Furthermore, the time for retaking may be minimized, in comparison to the case where all the images have to be taken again due to the failure of breath holding after all the imaging operations are finished, and therefore the imaging time can be reduced.

The configuration, operations and effects of the second embodiment other than those described above, are the same as those of the first embodiment, and therefore tedious explanations will not be made.

Figure 10:
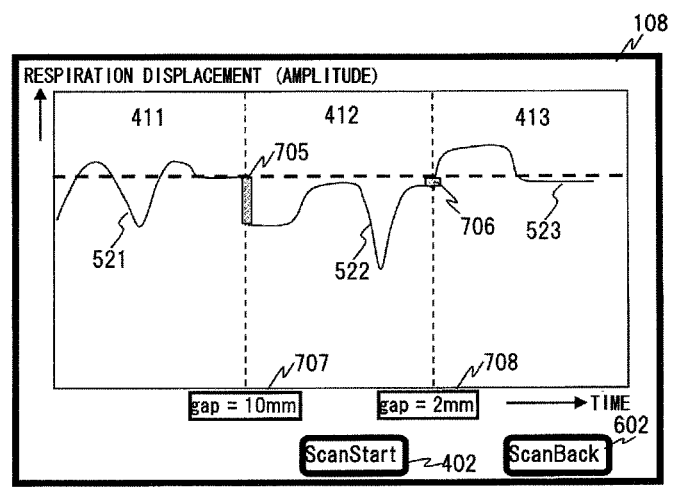
FIG. 10 illustrates on the monitor 108 in the second embodiment, an image showing respiratory waves, a difference in respiratory displacement between immediately before and immediately after the real imaging sequence, and the "Scan Back" button 602 used by the operator for instructing a retake when the operator determines that the breath holding has failed.

In the second embodiment, reconstructed images 611 to 614 are generated from the echo signals obtained in the real imaging sequences respectively and these images are displayed, and then, the operator determines whether or not there has been any failure in breath holding according to existence or non-existence of image degradation. It is further possible to configure, as shown in FIG. 10, such that the operator determines whether or not there is any failure in breath holding during the real imaging, according to an amount of displacement in waveforms of the respiratory waves 521 to 523. In other words, in the images 411 to 413 of the respiratory waves 521 to 523 of the navigator echoes generated and displayed in the steps 23 and 24, there are displayed gauges, respectively indicating the displacement amount 705 of the respiratory waves immediately before and after the first real imaging sequence and the displacement amount 706 of the respiratory waves immediately before and after the second real imaging sequence. Those displacement amounts 705 and 706 are indicated as numerical values in the regions 707 and 708, respectively, on the displayed screen. It is to be noted that these gauges and numerical values may be displayed after executing an initial sequence of the second navigator sequence or the third navigator sequence. The operator determines whether or not a retake is performed based on those information items above, and in the step 71, if the retake is performed, the operator presses the "Scan Back" button 602. If the operation proceeds to the next imaging, the operator presses the "Scan Start" button 402.

It is to be noted that the reconstructed images in the step 71 may be displayed together with the display of FIG. 10.

Third Embodiment

The third embodiment will be explained. In the third embodiment, the measurement controller 111 uses the displacement amounts 707 and 708 in FIG. 10 to automatically determine the necessity of retaking in the real imaging sequence.

Figure 11:
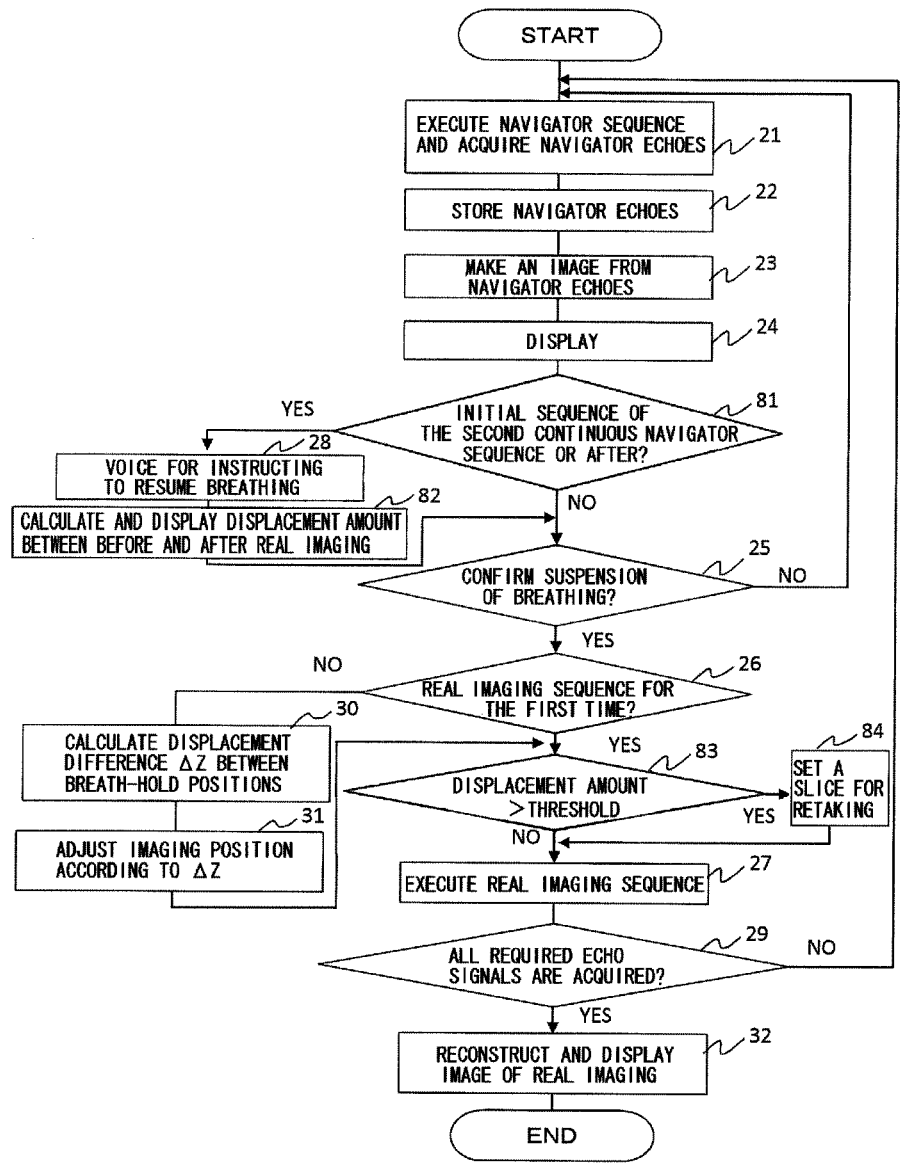
FIG. 11 is a flowchart showing the overall processing of the imaging operation of the third embodiment.
Figure 12:
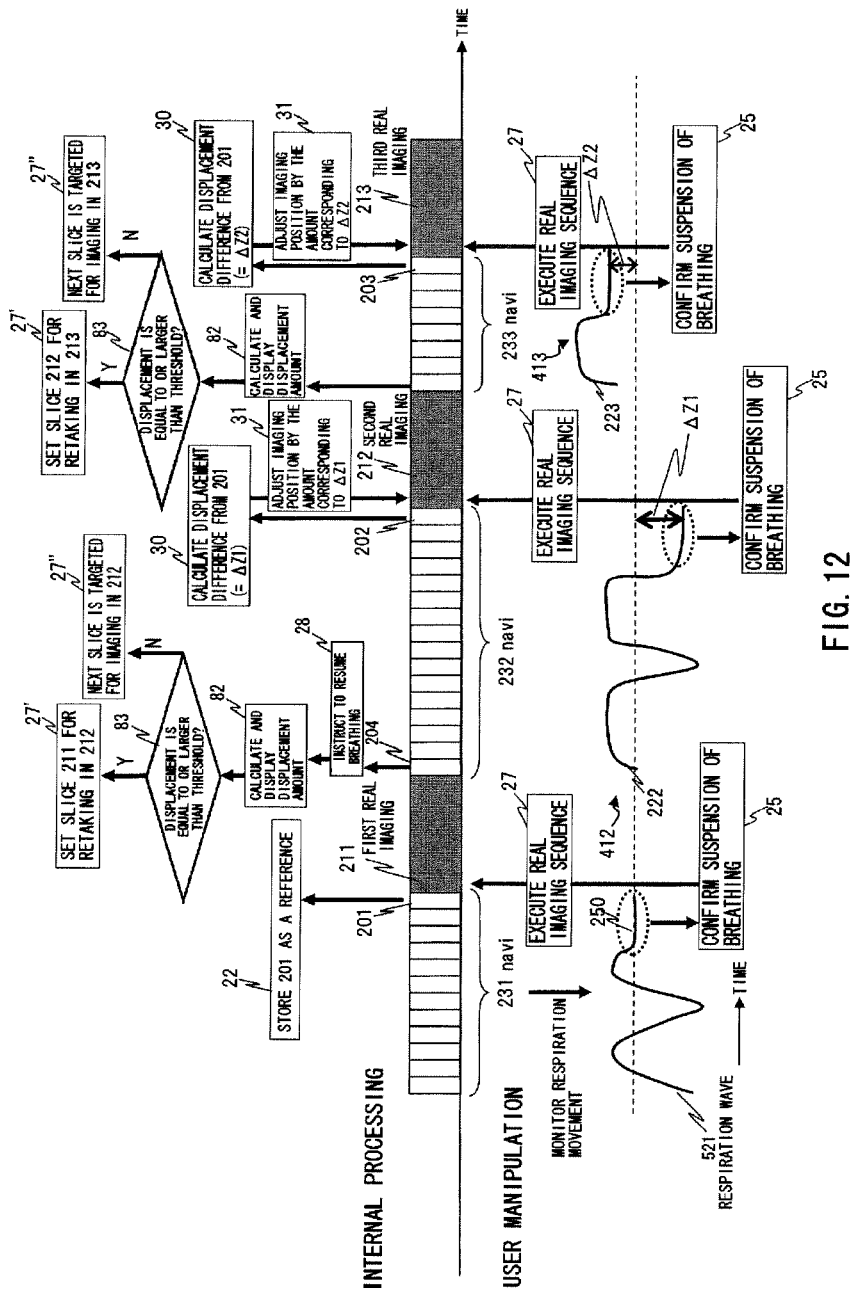
FIG. 12 illustrates a relationship in the third embodiment, among operations within the MRI device such as the navigator sequence and the real imaging sequence, respiratory displacement detected by navigator echoes, and manipulations by the user.

FIG. 11 is a flowchart illustrating the overall operation of the imaging method according to the third embodiment. FIG. 12 illustrates a relationship among operations within the device such as the navigator sequence and the real imaging sequence, respiratory displacement detected by navigator echoes, and manipulations by the user. In those figures, the configuration and processing being the same as those in the first and the second embodiment are labeled the same.

Figure 13:
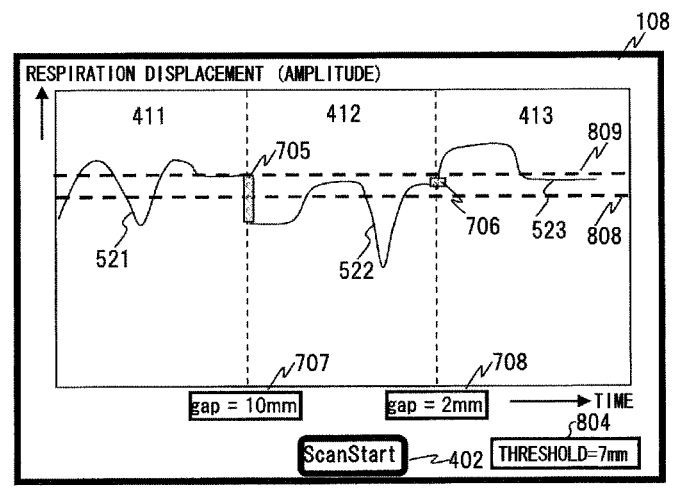
FIG. 13 illustrates on the monitor 108 in the third embodiment, an image showing respiratory waves and a difference in respiratory displacement between immediately before and immediately after the real imaging sequence, and a threshold used for determining a failure of the breath holding based on the difference in respiratory displacement.

As shown in FIG. 11 and FIG. 12, resumption of breathing is instructed to the subject 101, after the first real imaging sequence 211 is finished and at the timing when a navigator echo is acquired in the initial sequence 204 of the second continuous navigator sequence 232 (steps 81 and 28). The displacement amount 705 between this navigator echo being acquired and the navigator echo of the last sequence 201 of the first continuous navigator sequence 231 is calculated, and as shown in FIG. 13, it is displayed as a numerical value in the region 707 (step 82).

Thereafter, while the continuous navigator sequence 232 is repeated, the operator instructs the subject 101 to hold breathing, confirms that the breath is suspended based on the respiratory wave 522 of the image 912 on the monitor 108, and instructs by the "Scan Start" button 902 in the screen of the monitor 108 to start the second real imaging sequence 212 (step 25). Upon accepting the instruction, the measurement controller 111 determines whether or not the displacement amount 705 obtained in the step 82 is larger than a threshold (step 83), and when it is larger than the threshold, it is determined that the breath holding fails in the first real imaging sequence 211, and the operation proceeds to the step 84. Then, the slice being the same as the first real imaging sequence 211 is set and the real imaging sequence 212 for retaking is executed (step 27). In the step 83, if the displacement amount 705 is equal to or less than the threshold, a retake is unnecessary, and thus the next slice is set to execute the real imaging sequence 212 (step 27). This operation is repeated until all the echo signals necessary for reconstructing images of all the slices are obtained (step 29).

As the threshold used in the step 83, it is possible to configure such that the measurement controller 111 automatically sets the threshold with reference to a slice thickness. By way of example, the threshold may be set as 50% of the slice thickness. It is further possible to configure such that the operator sets any numerical value in the region 804 on the monitor 108, or the threshold is set to be an optional value by shifting the bars 808 and 809 on the screen with the use of a mouse or the like, the bars being shown on the images 411 to 413.

As thus described, in the configuration of the third embodiment, the measurement controller 111 is able to automatically recognize a failure of breath holding and perform a retake, and therefore, this may reduce the burden on the operator.

The configuration, operations and effects of the third embodiment other than those described above are the same as those of the first embodiment and the second embodiment.

According to the aforementioned present invention, it is possible to confirm that breathing of the subject is suspended before starting the breath-hold imaging, without using the gate window. Therefore, even in the case where the breath holding fails, a retake is possible in the middle of imaging, enabling easy reacquisition of minimum required data. In addition, in the case where there is a difference in respiratory displacement between the breath holding points, it is possible to compensate for the slice displacement corresponding to the difference in displacement. Furthermore, since any gate window is not used, the subject is allowed to perform breath holding at any position, and this reduces the burden on the subject.

EXPLANATION OF REFERENCES

101: subject, 102: static magnetic field magnet, 103: gradient coil, 104: RF coil, 105: RF probe, 106: signal detector, 107: signal processor (image reconstruction part), 108: monitor, 109: gradient power supply, 110: RF transmitter, 111: measurement controller, 112: bed

What is claimed is:

1. A magnetic resonance imaging device comprising,
 a static magnetic field generator which generates a static magnetic field in imaging space where a subject is placed,
 a gradient magnetic field generator which applies a gradient magnetic field to the imaging space,
 a radio frequency emitter which irradiates the imaging space with an RF magnetic field pulse,
 a receiver which receives a nuclear magnetic resonance signal generated from the subject, and
 a controller which controls the gradient magnetic field generator, the radio frequency emitter, and the receiver, so as to execute predetermined pulse sequences, wherein the pulse sequences includes a navigator sequence for detecting respiratory displacement of the subject, and a real imaging sequence for taking an image of the subject,
 the controller executing one or more programs of instructions to configure the controller to comprise:

a respiratory movement image generator which generates and displays an image showing a temporal change of respiratory displacement based on nuclear magnetic resonance signals acquired by executing the navigator sequence, a breath-hold confirmation accepting part which accepts a confirming operation from a operator when the operator views the image displayed by the respiratory movement image generator and confirms a state of breath holding, a real imaging execution part which executes the real imaging sequence at the timing when the breath-hold confirmation accepting part accepts the confirming operation, and a retake accepting part which obtains and displays a difference in respiratory displacement between, for each real imaging sequence that is repeated more than once, immediately before and after the real imaging sequence, and accepts from the operator an instruction whether or not a retake is performed as to the real imaging sequence for the present time, and upon accepting the instruction for the retake, the retake accepting part sets the imaging position of the real imaging sequence for the present time as the imaging position of the next real imaging sequence.

2. The magnetic resonance imaging device according to claim 1, wherein,
the controller allows operations by the respiratory movement image generator, the breath-hold confirmation accepting part, and the real imaging execution part, to be repeated more than once in this order, respectively, until all the nuclear magnetic resonance signals necessary for reconstructing an image of a predetermined imaging area are obtained by the real imaging sequence.

3. The magnetic resonance imaging device according to claim 2, wherein,
the controller obtains a difference in respiratory displacement acquired immediately before each of the real imaging sequences performed repeatedly more than once, and the controller adjusts an imaging position of the second and subsequent real imaging sequences, according to the difference.

4. The magnetic resonance imaging device according to claim 2, wherein the controller determines whether or not the breath holding is performed successfully during the real imaging sequence for said each real imaging sequence performed repeatedly more than once, and upon determining a failure of the breath holding, the imaging position of the real imaging sequence for the present time is set as the imaging position of the real imaging sequence for the next time.

5. The magnetic resonance imaging device according to claim 4, wherein when the controller determines that the difference in respiratory displacement between immediately before and immediately after the real imaging sequence is larger than a predetermined threshold, the controller determines the failure of the breath holding during the real imaging sequence.

6. A magnetic resonance imaging method, in a magnetic resonance imaging apparatus including a controller executing one or more programs of instructions to control the magnetic resonance imaging apparatus to perform the magnetic resonance imaging method, comprising a first step and a second step, both steps of which are repeated more than once until obtaining all the nuclear magnetic resonance signals necessary for reconstructing an image of a predetermined imaging area by a real imaging sequence, wherein
the first step generates and displays an image showing a temporal change of respiratory displacement of a subject based on the nuclear magnetic resonance signals acquired by executing a navigator sequence repeatedly on the subject, and the second step switches from the navigator sequence to the real imaging sequence to perform the real imaging sequence for a predetermined period of time, upon accepting from an operator a confirming operation that the operator views the image and confirms a state of breath holding, and wherein the magnetic resonance imaging method further comprises:

obtaining and displaying a difference in respiratory displacement between, for each real imaging sequence repeated more than once, immediately before and after the real imaging sequence, and accepting from the operator an instruction whether or not a retake is performed as to the real imaging sequence for the present time, and upon accepting the instruction for the retake, setting the imaging position of the real imaging sequence for the present time as the imaging position of the next real imaging sequence.

7. The magnetic resonance imaging method according to claim 6, the second step determines whether or not the breath holding is successfully performed during the real imaging sequence based on a difference in respiratory displacement between immediately before and immediately after the real imaging sequence, and upon determining a failure of the breath holding, second step performs a retake by the next real imaging sequence at the imaging position of the real imaging sequence for the present time.

8. The magnetic resonance imaging device according to claim 3, wherein the controller determines whether or not the breath holding is performed successfully during the real imaging sequence for said each real imaging sequence performed repeatedly more than once, and upon determining a failure of the breath holding, the imaging position of the real imaging sequence for the present time is set as the imaging position of the real imaging sequence for the next time.

9. The magnetic resonance imaging device according to claim 8, wherein when the controller determines that the difference in respiratory displacement between immediately before and immediately after the real imaging sequence is larger than a predetermined threshold, the controller determines the failure of the breath holding during the real imaging sequence.

* * * * *